United States Patent
Dolla et al.

(10) Patent No.: US 10,052,197 B2
(45) Date of Patent: Aug. 21, 2018

(54) ACCOMMODATIVE, CURVATURE-CHANGING INTRAOCULAR LENSES

(71) Applicant: NOVARTIS AG, Basel (CH)

(72) Inventors: William J. S. Dolla, Irving, TX (US); Parag Gupta, Grand Prairie, TX (US); Liezhi Liang, Los Angeles, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/819,863

(22) Filed: Aug. 6, 2015

(65) Prior Publication Data

US 2016/0157996 A1 Jun. 9, 2016

Related U.S. Application Data

(60) Provisional application No. 62/089,343, filed on Dec. 9, 2014.

(51) Int. Cl.
*A61F 2/16* (2006.01)

(52) U.S. Cl.
CPC .......... *A61F 2/1635* (2013.01); *A61F 2/1648* (2013.01); *A61F 2002/16901* (2015.04)

(58) Field of Classification Search
CPC ............................ A61F 2/1624; A61F 2/1635
See application file for complete search history.

(56) References Cited

U.S. PATENT DOCUMENTS

| | | | |
|---|---|---|---|
| 4,562,600 A | 1/1986 | Ginsberg et al. | |
| 7,569,073 B2 | 8/2009 | Vaudant et al. | |
| 7,753,953 B1 | 7/2010 | Yee | |
| 2002/0138140 A1 | 9/2002 | Hanna | |
| 2003/0135272 A1 | 7/2003 | Brady et al. | |
| 2004/0059414 A1 | 3/2004 | Green | |
| 2004/0082993 A1* | 4/2004 | Woods | A61F 2/1613 623/6.28 |
| 2005/0107875 A1 | 5/2005 | Cumming | |
| 2008/0154362 A1 | 6/2008 | Cumming | |
| 2008/0188930 A1 | 8/2008 | Mentak et al. | |
| 2009/0228102 A1 | 9/2009 | Pynson | |

(Continued)

FOREIGN PATENT DOCUMENTS

WO 20140152017 A1 9/2014

OTHER PUBLICATIONS

PCT/US2015/044015, International Search Report, International Searching Authority (US), dated May 12, 2016, 4 pgs.

*Primary Examiner* — Leslie Lopez

(57) ABSTRACT

The present disclosure concerns a curvature-changing, accommodative intraocular lens (IOL) that may be implanted in the capsular bag of a patient's eye and is configured to harness the energy of the movement of the capsular bag upon contraction and relaxation of the ciliary muscles. In certain embodiments, the IOL includes a fluid optic body defining a cavity for containing an optical fluid, the cavity at least partially defined by a first optical membrane configured to extend across an optical axis of the patient's eye. The IOL further includes a plurality of lever arms extending from the optic body and configured to be in contact with the capsular bag such that axial compression of the capsular bag causes each of the plurality of lever arms to rotate about a corresponding pivot so as to modify a curvature of the first optical membrane.

13 Claims, 9 Drawing Sheets

(56) References Cited

U.S. PATENT DOCUMENTS

| | | |
|---|---|---|
| 2010/0179653 A1 | 7/2010 | Argento et al. |
| 2011/0130833 A1 | 6/2011 | Scott et al. |
| 2011/0295367 A1 | 12/2011 | Cuevas |
| 2012/0330415 A1 | 12/2012 | Callahan et al. |
| 2013/0197635 A1 | 8/2013 | Phillips |
| 2013/0231741 A1 | 9/2013 | Clarke |
| 2013/0304203 A1 | 11/2013 | Beer |
| 2014/0052246 A1 | 2/2014 | Kahook et al. |

\* cited by examiner

ACCOMMODATIVE, CURVATURE-CHANGING INTRAOCULAR LENSES

This application claims the priority of U.S. Provisional Application No. 62/089,343 filed Dec. 9, 2014 which is hereby incorporated herein by reference in its entirety.

FIELD

This present disclosure relates generally to the field of intraocular lenses (IOLs) and, more particularly, to accommodative IOLs.

BACKGROUND

The human eye in its simplest terms functions to provide vision by receiving light through a clear outer portion called the cornea, and focusing the image by way of a crystalline lens onto a retina. The quality of the focused image depends on many factors including the size and shape of the eye, and the transparency and focal power of the cornea and the lens.

When age or disease causes the lens to become less transparent, vision deteriorates because of the diminished amount of light that is transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by zonules. Relaxation of the ciliary muscle applies an axial force that tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus on both near and far objects.

As the lens ages, it becomes harder and is less able to change shape in response to movements of the ciliary muscle. This makes it harder for the lens to focus on near objects, a medical condition known as presbyopia. Presbyopia affects nearly all adults by the age of 45 or 50.

When a cataract or other disease requires the removal of the natural lens and replacement with an artificial IOL, the IOL typically is a monofocal lens that provides a suitable focal power for distance vision but requires the use of a pair of spectacles or contact lenses for near vision. Multifocal IOLs, e.g., relying on diffractive patterns to general multiple foci, have been proposed but to date have not been widely accepted.

Therefore, a need exists for a safe and stable accommodative intraocular lens that provides accommodation over a broad and useful range.

SUMMARY

The present disclosure concerns curvature-changing, accommodative intraocular lenses (IOLs) that may be implanted in the capsular bag of a patient's eye and configured to harness the energy of the movement of the capsular bag upon contraction and relaxation of the ciliary muscles. In certain embodiments, the IOLs described herein are designed such that axial compression of the capsular bag rotates a plurality of lever arms (which may also be referred to as haptics) at least partially in contact with the capsular bag such that a fluid-filled cavity defined in part by a deformable optical membrane changes shape, thereby altering the curvature of the membrane and the power of the optic. For example, when the ciliary muscles relax such that the fibrous zonules extending between the ciliary muscles and the capsular bag become taut, the capsular bag is axially compressed. This axial compression of the capsular bag may cause the lever arms to rotate about corresponding pivots in a manner that reduces the curvature of the deformable optical membrane (as in a native lens during disaccommodation). Conversely, when the ciliary muscles contract such that the tension of the fibrous zonules extending between the ciliary muscles and the capsular bag is reduced, axial compression of the capsular bag may be reduced. This reduction in axial compression of the capsular bag may also cause the lever arms to rotate about the corresponding pivots (e.g., in a direction opposite that discussed above) in a manner that increases the curvature of the deformable optical membrane (as in a native lens during accommodation). Therefore, certain embodiments of the present disclosure may provide an accommodative IOL that can be implanted into the native capsular bag to replace a cataractous or presbyopic natural crystalline lens removed therefrom.

In certain embodiments, an IOL includes a fluid optic body defining a cavity for containing an optical fluid, the cavity at least partially defined by a first optical membrane configured to extend across an optical axis of the patient's eye. The IOL further includes a plurality of lever arms extending from the optic body and configured to be in contact with the capsular bag such that axial compression of the capsular bag causes each of the plurality of lever arms to rotate about a corresponding pivot so as to modify a curvature of the first optical membrane.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

The skilled person in the art will understand that the drawings, described below, are for illustration purposes only. The drawings are not intended to limit the scope of the applicant's disclosure in any way.

DETAILED DESCRIPTION

Figure 1:
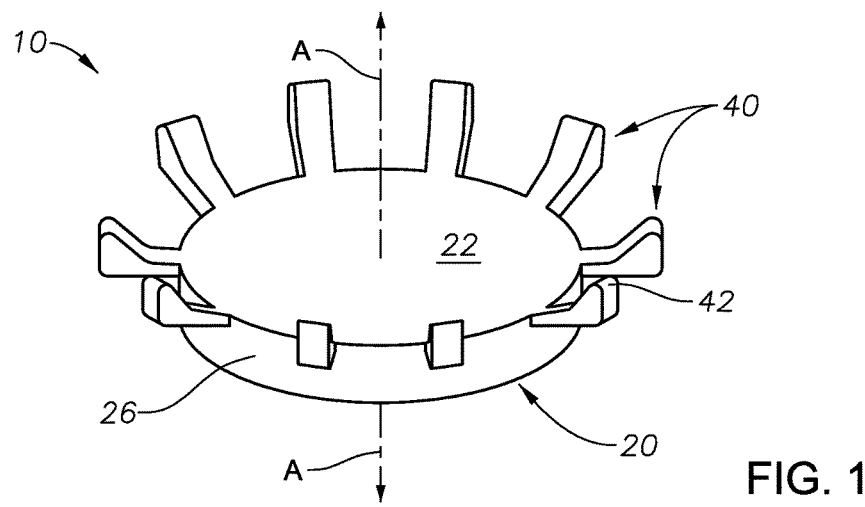
FIG. 1 is a perspective view of an exemplary curvature-changing, accommodative intraocular lens, according to certain embodiments of the present disclosure.
Figure 2:
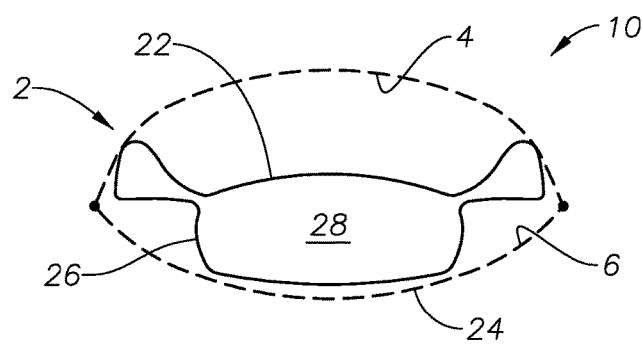
FIG. 2 is a cross-sectional view of the exemplary lens of FIG. 1, depicting the lens in its accommodated (close vision) state.
Figure 3:
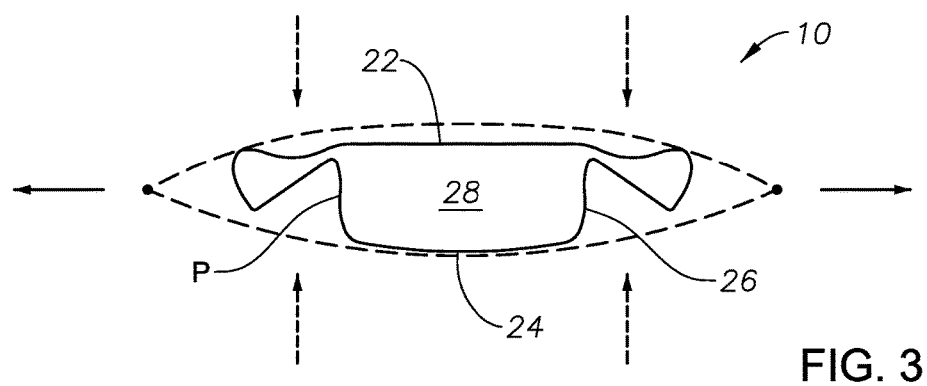
FIG. 3 is a cross-sectional view of the exemplary lens of FIG. 1, depicting the lens in its disaccommodated (near vision) state.

The present disclosure generally relates to an intraocular lens (IOL) configured to be implanted in the capsular bag of a patient and that can utilize the movement of the capsular bag to change the power of the IOL. With reference to FIGS. 1-3, an exemplary IOL 10 is depicted in accordance with various aspects of the present disclosure. As shown in FIG. 1, the IOL 10 generally comprises a central optic body 20 configured to be disposed on the optical axis (A) of the patient's eye such that light traversing the optic body 20 can be refracted thereby. The IOL 10 additionally includes a plurality of lever arms 40 that extend from the optic body 20 and that can rotate around corresponding pivots in response to movement of the capsular bag 2 during accommodation/disaccommodation. As a result, the shape of the optic body 20 may be changed and the optical power of the IOL 10 altered.

The central optic body 20 can have a variety of configurations but generally comprises a sealed cavity for containing an optical fluid, the sealed cavity being at least partially defined by a deformable optical membrane. As shown in FIG. 2, the central optic body 20 comprises a deformable optical membrane 22, a second optical membrane 24, and a circumferential sidewall 26 extending therebetween such that a sealed cavity 28 (which may contain an optical fluid) is formed within the optic body 20. As discussed in detail below, the sidewall 26 can be coupled to the deformable optical membrane 22 such that rotation/flexion of at least a portion of the sidewall 26 increases tension on the deformable optical membrane 22. Although the deformable optical membrane 22 is depicted and described herein as being located anterior to the second optical membrane 24 when disposed within the capsular bag 2 (such that the second optical membrane 24 contacts at least a portion of a posterior surface 6 of the capsular bag 2), the present disclosure contemplates that an IOL 10 may alternatively be configured such that, when implanted within the capsular bag 2, the deformable membrane 22 may be located posterior to the deformable membrane 22 (such that the second optical membrane 24 contacts at least a portion of an anterior surface 4 of the capsular bag 2).

The optic body 20 of IOL 10 may comprise a variety of materials that include, for example, fluid impermeable and biocompatible materials. In particular, the deformable optical membrane 24 and the second optical membrane 24 may each be constructed of materials that are optically transparent and smooth (e.g., an optical-quality surface). Exemplary materials include hydrogels, silicones, acrylic materials, and other elastomeric polymers and soft plastics. For example, the silicone materials can be unsaturated terminated siloxanes, such as vinyl terminated siloxanes or multi-vinyl terminated siloxanes. Non-limiting examples include vinyl terminated diphenylsiloxane-dimethylsiloxane copolymers, vinyl terminated polyphenylmethylsiloxanes, vinyl terminated phenylmethylsiloxane-diphenyidimethylsiloxane copolymers, vinyl terminated polydirnethylsiloxanes and methacrylate, and acrylate functional siloxanes. In other embodiments the lens-forming materials can be a hydrogel or a hydrophobic acrylic, such as the AcrySof® acrylic. Use of elastic/flexible materials can also enable the IOL 10 or optic body 20 to be folded upon itself during implantation, thereby decreasing the size of the incision required to insert the IOL 10 into the capsular bag 2.

In certain embodiments, the optic body 20 may comprise a unitary body in which the deformable optical membrane 24, the second optical membrane 24, and the sidewall 26 are continuous and formed of the same material, though different portions of the optic body 20 may vary in thickness in order to provide the desired movement of the optic body 20, as otherwise discussed herein. For example, the second optical membrane 24 may be thicker relative to the sidewall 26 and the deformable optical membrane 22. As such, the second optical membrane 24 may provide structural support for the IOL 10 upon axial compression thereof, while the sidewall 26 may flex or rotate in response to the axial force on the lever arms 40 (thereby tensioning/stretching the relatively thin/elastic deformable optical membrane 22).

In certain embodiments, different portions of the optic body 20 may be constructed of materials having varying stiffness in order to provide the desired movement of the optic body 20, as otherwise discussed herein. For example, the deformable optical membrane 22 may be constructed of an elastomeric material having a low modulus, while the second optical membrane 24 may be constructed of a more rigid material.

Optic body 20 of IOL 10 may have any suitable configuration facilitating accommodation as described herein. For example, optic body 20 may be substantially cylindrical (e.g., having substantially circular optical membranes 22, 24 and a sidewall 26 extending in the direction of the optical axis (A) therebetween), as depicted in FIGS. 1-3. Alternatively, optic body 20 may have a non-circular cross section across the optical axis (e.g., of oval or elliptical cross-section). Additionally, the sidewall 26 of optic body 20 may have any suitable configuration that facilitates rotation/flexion in response to movement of the lever arms 40 (e.g., rotation of lever arms 40 about corresponding pivot points/areas located on or about sidewall 26). For example, the sidewall 26, when viewed in cross section, may provide a concave connection (relative to the optical axis (A)) between deformable membrane 22 and second optical membrane 24 when in the accommodated state (as shown in FIG. 2), and axial compression of the capsular bag 2 may cause rotation of lever arms 40, thereby causing deformation of sidewall 26 (e.g., at least an anterior portion of the sidewall may rotate about the midpoint (P) of sidewall 26 and/or the radius of curvature of the sidewall 26 may increase, as shown in FIG. 3). In embodiments in which the sidewall 26 is arched, the force necessary to flex the sidewall and deform the optical membranes may be reduced, stress concentration at a single pivot point may be avoided, manufacture (e.g., molding) may be eased, and the useful lifespan of the IOL may be increased. Alternatively, the sidewall 26, when viewed in cross section, may provide a substantially straight connection between deformable membrane 22 and second optical membrane 24 (e.g., parallel to the optical axis (A)), as discussed below with reference to FIG. 9.

The optical fluid contained within the cavity 28 of IOL 10 may be any suitable fluid and may include, for example, an incompressible or substantially incompressible fluid exhibiting an index of refraction different that the fluid surrounding the IOL 10. As a result, light passing through the IOL 10 may undergo refraction at both the deformable optical membrane 22 and the second optical membrane 24, the level of refraction being dependent upon the shape of the boundary between the optical fluid and the external fluid (i.e., the shape of the deformable optical membrane 22 and the second optical membrane 24 relative to the optical axis(A)). Exemplary suitable fluids for use in the cavity 28 include fluids with an index of refraction higher than water, for example, an index of refraction greater than 1.3. In certain embodiments, the fluid may exhibit an index of refraction greater than 1.36 or greater than 1.38. In other embodiments, the index of refraction may be in the range of about 1.3 to about 1.8, in the range of about 1.36 to about 1.70, or in the range of about 1.38 to about 1.60. Suitable fluids may include saline, hydrocarbon oils, silicone oils, and silicone gels.

The optical fluid may be disposed within the cavity 28 during fabrication of the IOL 10, after fabrication but before implantation of the IOL 10, or after implantation of the IOL 10. For example, the optic body 20 may include a fill port that can be sealed or plugged after filling the cavity 28. Additionally or alternatively, the optical fluid may be injected through the optic body 20 and the optic body 20 may be self-sealing.

The plurality of lever arms 40 of IOL 10 may have any suitable configuration operable to contact the capsular bag 2 upon implantation and rotate about corresponding pivots when compressed by the capsular bag 2, as described in detail below. For example, as shown in FIG. 1, IOL 10 may include a plurality of lever arms 40 each extending radially from the circumference of the optic body 20 at a location adjacent the anterior to deformable optical membrane 22. Although a particular number of lever arms 40 are depicted, the present disclosure contemplates that IOL 10 may have any suitable number of lever arms 40.

At least a portion of each lever arm 40 may extend radially beyond the sidewall 26 and may include an anterior surface 42. At least a portion of anterior surface 42 may contact the anterior surface 4 of the capsular bag 2 upon implantation. The anterior surface 42 of the lever arms 40 can have any suitable shape facilitating the functionality described herein. For example, anterior surface 42 may be curved so as to maintain good contact with the capsular bag 2 during axial compression. As is illustrated by FIGS. 2-3, the portion of the anterior surface 42 of a lever arm 40 in contact with the capsular bag 2 may change as the capsular bag 2 changes shape. In particular, the capsular bag 2 may contact a more peripheral portion of the lever arm 40 when the capsular bag is in a relaxed state (as illustrated in FIG. 2) than when the capsular bag 2 is in an axially compressed state (as illustrated in FIG. 3). The present disclosure contemplates that the shape of the anterior surface 42 of lever arms 40 (or other portions of lever arms 40) may be optimized to correspond to the shape of the capsular bag 2 as it changes during accommodation, thereby improving stability of the IOL 10 within the capsular bag 2, reducing slippage of the IOL 10, and/or maximizing the transfer of energy due to the movement of the capsular bag 2. Additionally, the present disclosure contemplates that lever arms 40 may have a variety of lengths or widths. For example, the lever arms 40 can have a length such that in its resting state, the IOL 10 can exhibit an outer diameter slightly larger than the maximum diameter of the capsular bag 2 such that the tension exerted by the capsular bag 2 on the lever arms 40 upon implantation substantially maintains the IOL 10 in a desired position within the capsular bag 2. Movement of the exemplary IOL 10 depicted in FIGS. 1-3 will now be described as the capsular bag 2 goes from an accommodated state (as shown in FIG. 2) to a disaccommodated state (as shown in FIG. 3). With reference first to FIG. 2, the IOL 10 and capsular bag 2 are depicted in their accommodated state during which the ciliary muscles are contracted such that zonules extending between the ciliary muscles and the capsular bag 2 are slack. As a result, there exists little radial tension on the capsular bag 2 such that the capsular bag 2 assumes a substantially round shape. Accordingly, though the lever arms 40 may be disposed in contact with the capsular bag 2, the capsular bag 2 may exert little or no axial force (i.e., force along the axis (A) depicted in FIG. 1) on the lever arms 40.

Upon relaxation of the ciliary muscles, the zonules will exert radial tension on the capsular bag 2 (as indicated by the solid arrows in FIG. 3), which causes axial compression of the capsular bag 2 (as indicated by the broken arrows). As a result, an axial force may be applied to the lever arms 40 in contact with the capsular bag 2 (e.g., in contact with an anterior surface 4 of the capsular bag 2). This axial force may cause rotation each of the lever arms 40 about a corresponding pivot, which may include any point or region of the optic body 20 about which a lever arm may rotate. Rotation of the lever arms 40 may in turn cause the upper portion of the sidewall 26 coupled thereto to flex or rotate, thereby exerting tension on the deformable optical membrane 22. Comparing FIGS. 2 and 3, it will be appreciated that, as a result of this radial and posterior (non-circumferential) rotation of lever arms 40 and sidewall 26, the deformable optical membrane 22 exhibits a flatter profile (e.g., a larger radius of curvature). For example, the diameter of the upper portion of the cavity 28 (i.e., distance between the sidewall 26 on opposed sides of the optical axis (A)) may increase as the sidewall 26 flexes outward, thereby pulling the deformable optical membrane 22 taut and decreasing the distance between the deformable optical membrane 22 and the second optical membrane 24 along the optical axis (A). As the radial force on the capsular bag 2 is relaxed, the capsular bag 2 and IOL 10 may return to a biased configuration shown in FIG. 2.

The above-described IOL 10 may be fabricated using any suitable techniques known in the art and modified in light of the present teachings. For example, IOL 10 may be injection molded such that the lever arms 40 and deformable optical membrane 22 are biased to a particular position (as shown in FIG. 2). That is, in the absence of substantial external forces (e.g., in its free form outside the eye), the IOL 10 can be configured to maintain a radius of curvature approximate its shape in an accommodated state. Accordingly, the lever arms 40 would tend to return to this biased position upon removal of or relaxation of the axial compressive force (e.g., as the capsular bag goes from its disaccommodated configuration to its accommodated configuration). This biased configuration may especially aid those patients in which the ciliary bodies have lost some of their contractility or the capsular bag 2 has lost some of its elasticity, for example, due to age.

Figure 4:
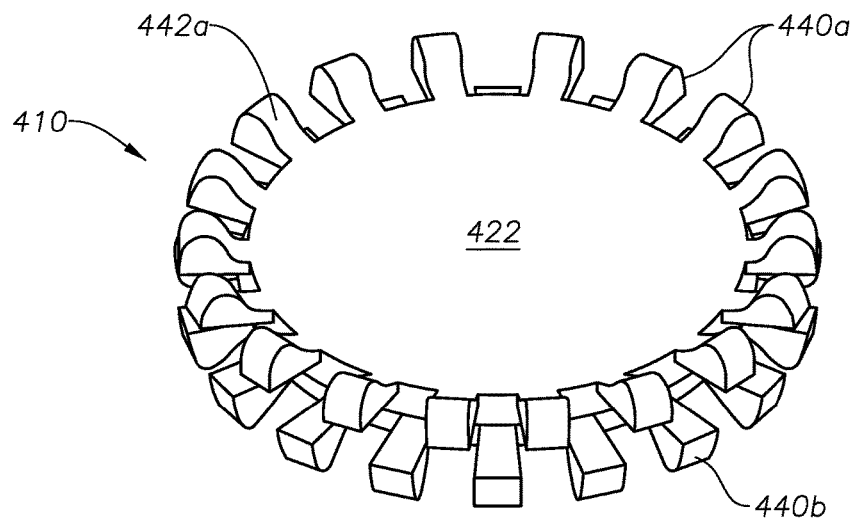
FIG. 4 is a schematic, perspective view of another exemplary curvature-changing, accommodative intraocular lens, according to certain embodiments of the present disclosure.
Figure 5:
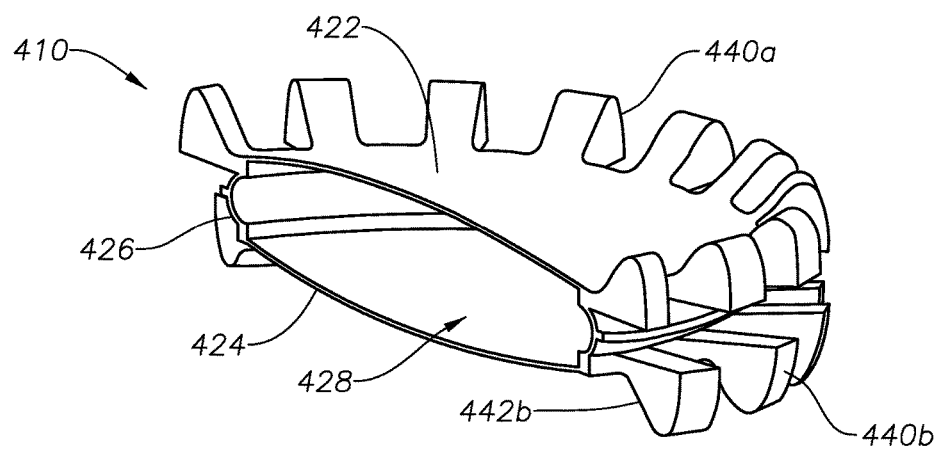
FIG. 5 is a perspective view of the exemplary lens of FIG. 4 in cross-section.
Figure 6:
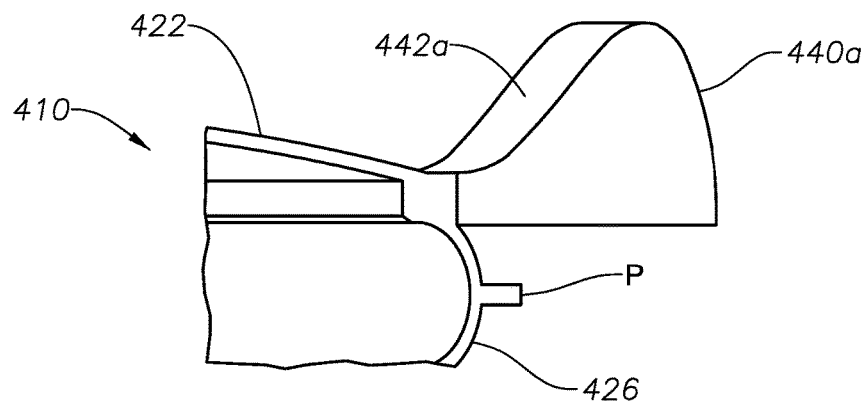
FIG. 6 is another view of the exemplary lens of FIG. 4 in cross-section.

With reference now to FIGS. 4-6, another exemplary IOL 410 is depicted. The IOL 410 is substantially similar to the IOL 10 depicted in FIGS. 1-3, but differs in that both of the optical membranes 422 and 424 of the optic body 420 are configured to deform in response to axial compression of the capsular bag. As shown in FIGS. 4 and 5, the IOL 410 may include a first set of lever arms 440a extending radially from the optic body 420 from a location adjacent the optical membrane 422 (anterior deformable optical membrane 422) and a second set of lever arms 440b extending radially from the optic body 420 from a location adjacent the optical membrane 424 (posterior deformable optical membrane 424). Thus, unlike the IOL 10 described above with reference to FIGS. 1-3 in which the posterior membrane 24 is configured to be disposed in direct contact with the posterior surface 6 of the capsular bag 2, IOL 410 can be disposed within the capsular bag such that at least a portion of the curved surface of each of the first set of lever arms 440a is disposed in contact with the anterior surface of the capsular bag, while at least a portion of the curved surface of each of the second set of lever arms 440b is disposed in contact with the opposed, posterior surface of the capsular bag. The first set of lever arms 440a and the second set of lever arms 440b may be substantially identical (except for their differing orientation). Alternatively, the first set of lever arms 440a and the second set of lever arms 440b may each be shaped in order to best match the shape of the portion of the capsular bag with which they will interact during movement thereof.

In IOL 410, both optical membrane 422 and optical membrane 424 may be deformable such that they both change shape in response to rotation of the corresponding sets of lever arms 440. The sidewall 426 extending between the first optical membrane 422 and the second optical membrane 424 can also be in the form of an arch and act as a pivot for the rotation of the lever arms 440, the radius of curvature of the arch increasing as (1) the first set of lever arms 440a flex the anterior-most portions of the sidewall 426 radially outward, and (2) the second set of lever arms 440b flex the posterior-most portions of the sidewall 426 radially outward. As such, the first set of lever arms 440a and the second set of lever arms 440b can both rotate (in opposed directions) about one or more pivots in response to axial compression of the capsular bag to harvest the energy of movement of both sides of the capsular bag, thereby potentially increasing the curvature change and ultimately the optical power change of the IOL 410. Although sidewall 426 is depicted and described as being configured as an arch, the present disclosure contemplates that sidewall 426 (like sidewall 26 discussed above with regard to FIGS. 1-3) may have any suitable configuration that facilitates rotation/flexion in response to movement of the lever arms 440. As discussed above, however, in embodiments in which the sidewall 426 is arched, the force necessary to flex the sidewall and deform the optical membranes may be reduced, stress concentration at a single pivot point may be avoided, manufacture (e.g., molding) may be eased, and the useful lifespan of the IOL may be increased.

As shown in FIGS. 4-5, the first set of lever arms 440a may be staggered circumferentially relative to the second set of lever arms 440b to avoid interference during rotation. In certain embodiments, the number of lever arms 440 in the IOL 410 may be increased relative to that of the exemplary IOL 10 depicted in FIGS. 1-3. In embodiments including a large number a lever arms 440 (e.g., greater than twelve lever arms 440) of relatively small size (relative to haptics that may be commonly used in the art), contact of the IOL 410 with the capsular bag may be increased. This may increase the amount of energy being harvested from the capsular bag, decrease localized deformation on the root of haptics on optical membranes 422 and 424 (associated with astigmatism), and/or improve implantation by reducing the size of the access incision necessary to accommodate the smaller lever arms 440.

Figure 7A:
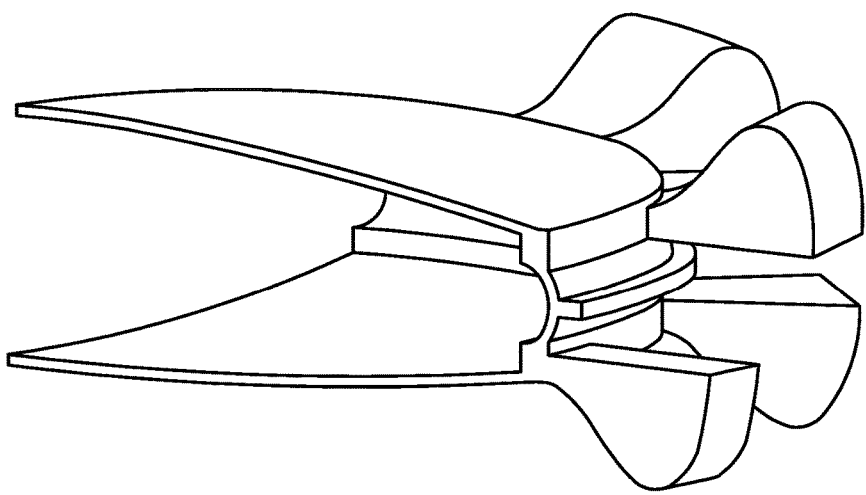
FIGS. 7A-D illustrate the movement of the lens of FIG. 4 from an accommodated state to a disaccommodated state.
Figure 7B:
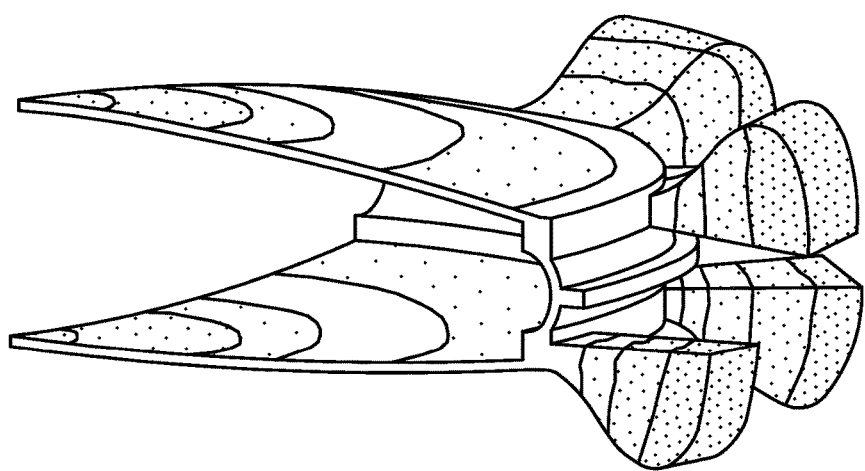
Figure 7C:
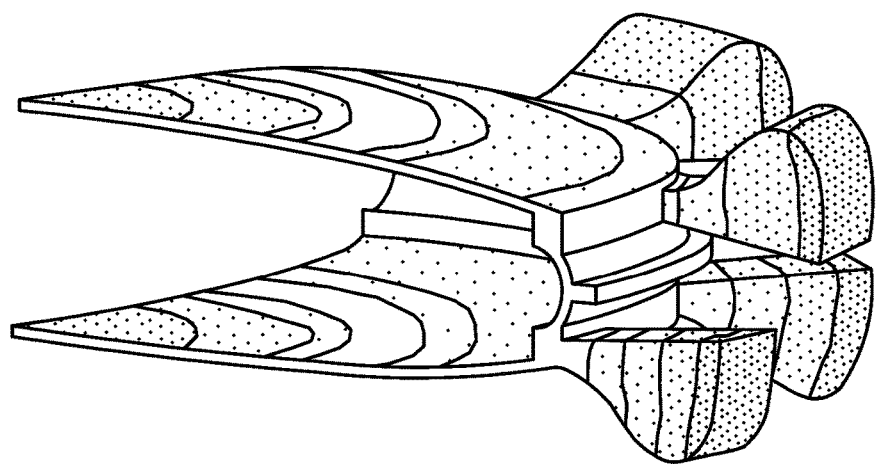
Figure 7D:
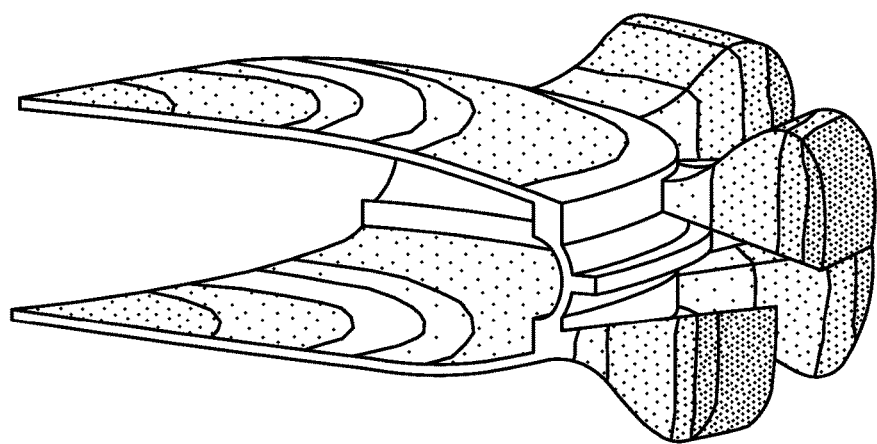

With reference now to FIG. 7, finite element analysis of exemplary simulated movement of the IOL 410 is depicted as the lens 410 moves from its resting or accommodated state (as shown in FIG. 7A) to its disaccommodated state (as shown in FIG. 7D). Upon axial compression of the capsular bag, the axial compressive forces on the lever arms 440 increase, initiating rotation of the lever arms 440 about corresponding pivots and the transfer of force to the optical membranes 422 and 424 (as shown in FIG. 7B). As compression continues, the lever arms 440 rotate further and the cavity 428 containing the optical fluid changes shape as optical membranes 422 and 424 become flatter (as depicted in FIGS. 7C and 7D).

Figure 8:
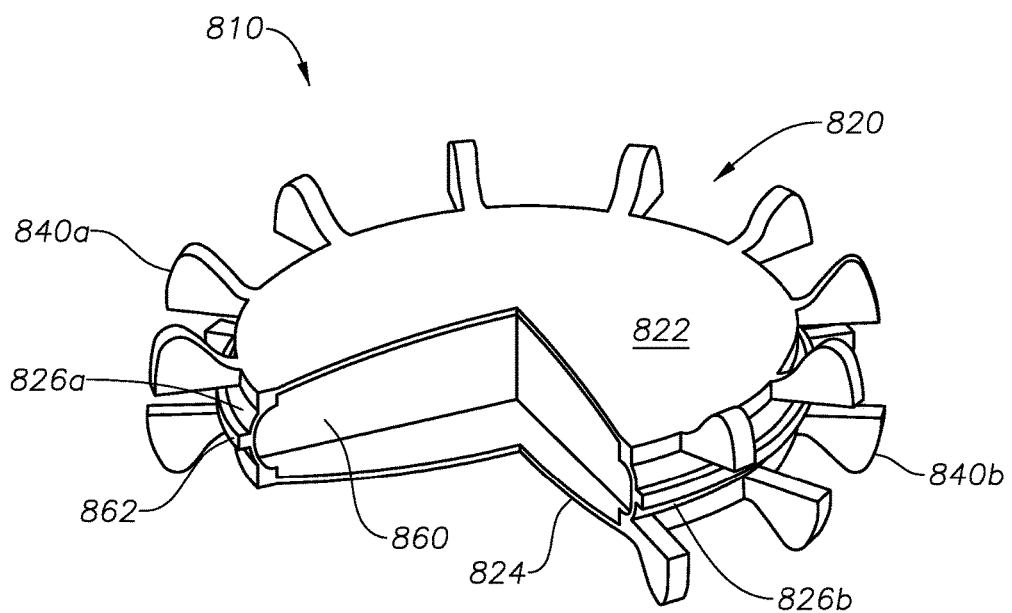
FIG. 8 is a perspective, partial cross-sectional view of another exemplary curvature-changing, accommodative intraocular lens, according to certain embodiments of the present disclosure.

With reference to FIG. 8, another exemplary IOL 810 is depicted. Like IOL 410 discussed above, IOL 810 comprises an optic body 820 having opposed deformable membranes 822 and 824 and a plurality of lever arms 840 (including a first set of lever arms 840a and a second set of lever arms 840b) extending therefrom. IOL 810 differs from IOL 410 in that a solid lens 860 is disposed between optical membranes 822 and 824. Whereas the curvature of optical membranes 822 and 824 can generally be used to control the power of the IOL 810, the solid lens 860 can additionally provide for power change or other features that may be known in the art (e.g., spherical, aspheric, toric features). The solid lens 860 may be disposed between the optical membranes 822 and 824 prior to implantation (e.g., within the cavity or sandwiched between the membranes), or the IOL 810 can be assembled in situ. In some aspects, the solid lens 860 and other portions of the IOL 810 may be inserted into the capsular bag separately and assembled therein, for example, by coupling the portion of the sidewall 826a extending posteriorly from the anterior optical membrane 822 to the periphery of the solid lens 860 (e.g., a circumferential shoulder 862 of the solid lens 860) or to the portion of the sidewall 826b extending anteriorly from the posterior optical membrane 824. For example, the surfaces can be coupled (e.g., welded, adhered, etc.) to one another so as to create a seal for containing optical fluid. One or more fluid cavities can thus be defined between the solid lens 860 and the optical membranes 822 and 824. To further aid delivery, the solid lens can also be elastomeric or foldable to ease insertion into the capsular bag.

Figure 9:
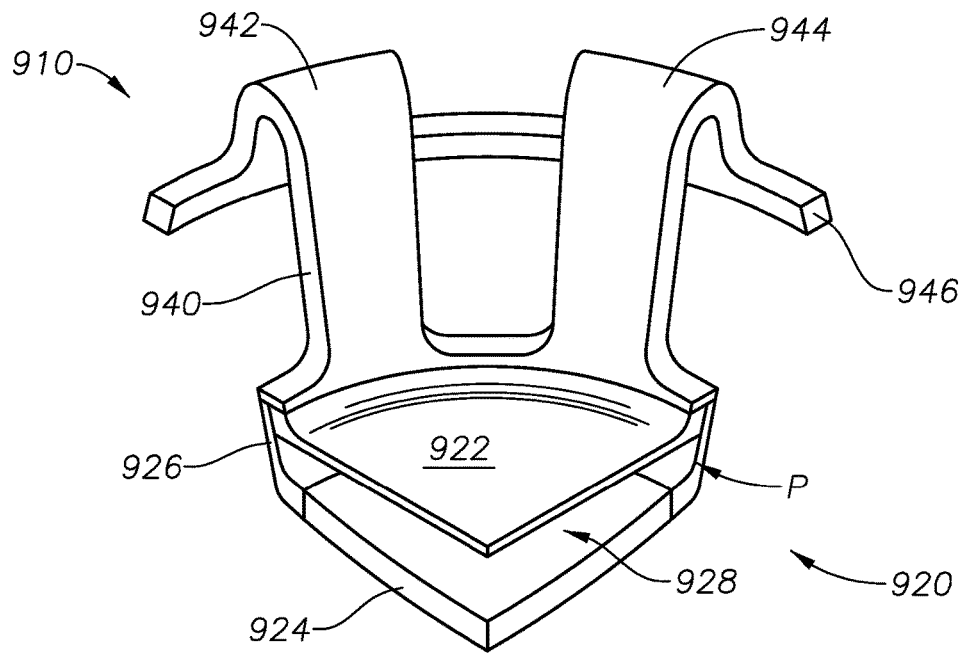
FIG. 9 is a perspective, partial cross-sectional view of another exemplary curvature-changing, accommodative intraocular lens, according to certain embodiments of the present disclosure.

With reference now to FIG. 9, another exemplary IOL 910 is depicted. IOL 910 is similar to the IOLs described above in that it utilizes the natural forces of the capsular bag during compression to drive the power change of the optic. As shown in FIG. 9, the exemplary optic body 920 comprises a deformable optical membrane 922, a second optical membrane 924, and a circumferential sidewall 926 extending therebetween such that a sealed fluid cavity 928 is formed within the optic body 920. The second optical membrane 924 can be the same or different material as the deformable optical membrane 922; however, it may be stiffer relative thereto so as to support the IOL 910 within the capsular bag. The IOL 910 can comprise a single, unitary structure (e.g., formed via injection molding) or can comprise portions of varying stiffness that can be coupled (e.g., bonded) together. For example, the deformable optical membrane 922 may be formed of a thin, elastomeric material having a low modulus, while the second optical membrane 924 may be formed of a more rigid material. Likewise, the sidewall 926 and lever arms 940 may have the appropriate stiffness so as to flex in accordance with the present teachings as otherwise discussed herein.

Like IOL 10 of FIGS. 1-3, IOL 910 may comprise a single set of lever arms 940 that extend therefrom. The lever arms 940 initially extend anteriorly and radially (though substantially along the optical axis) from the optic body 920 to an anterior most surface 942 that is configured to contact the anterior surface of the capsular bag, and then flare radially and posteriorly to a terminal end 944. As shown in FIG. 9, the terminal ends 944 of adjacent lever arms 940 may be coupled via a ring-like structure 946 disposed around the circumference of the IOL 910. Lever arm ring 946 may be effective to increase stability of the IOL 910 within the capsular bag and/or improve the uniformity of the force exerted on the deformable optical membrane 922 as the lever arms 940 coupled via the ring 946 rotate about corresponding pivots.

Figure 10:
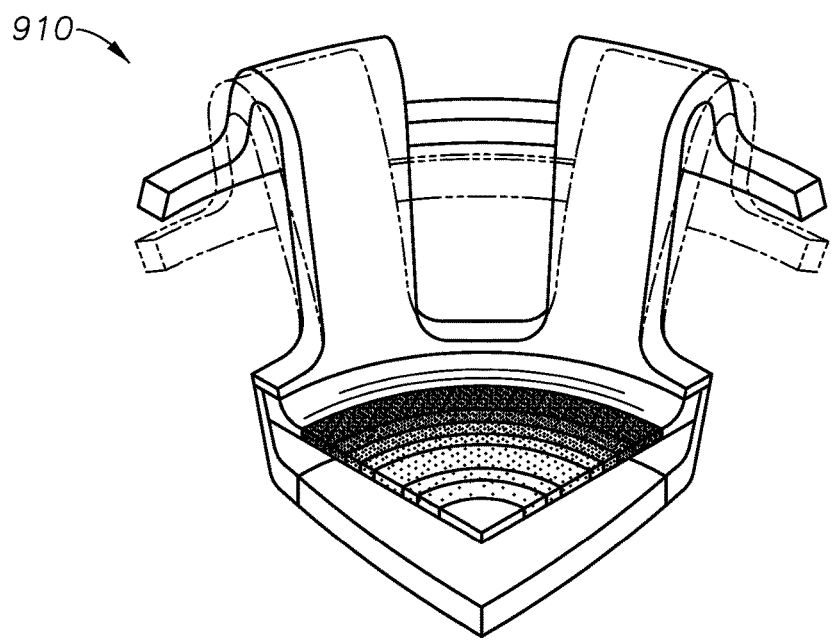
FIG. 10 schematically depicts the movement of the lens of FIG. 9 as it moves from an accommodated state to a disaccommodated state.

With reference now to FIG. 10, movement of the IOL 910 is depicted as the lens 910 moves from its resting or accommodated state (shown in phantom) to its disaccommodated state (shown in solid). As shown in FIG. 10, upon axial compression of the capsular bag, the axial compressive force on the lever arms 940 increases, flexing the lever arms 940 radially outward about a pivot, thereby increasing the stress on the deformable optical membrane 922 via its coupling thereto. As compression continues, the lever arms 940 rotate further and the cavity 928 containing the optical fluid changes shape as the deformable optical membrane 922 flattens.

Figure 11A:
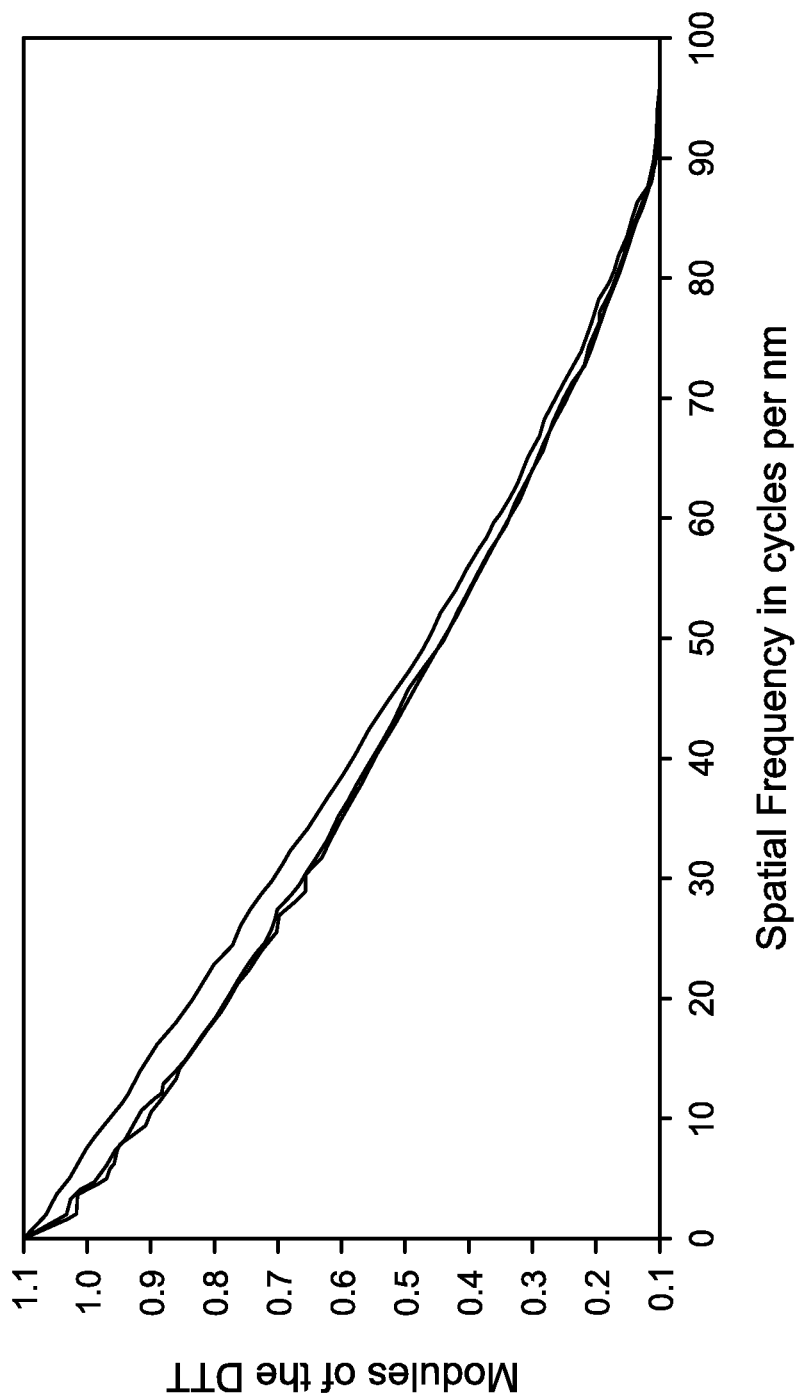
FIGS. 11A-C illustrate a simulation of the curvature change of the lens of FIG. 9 at various stages of axial compression.
Figure 11B:
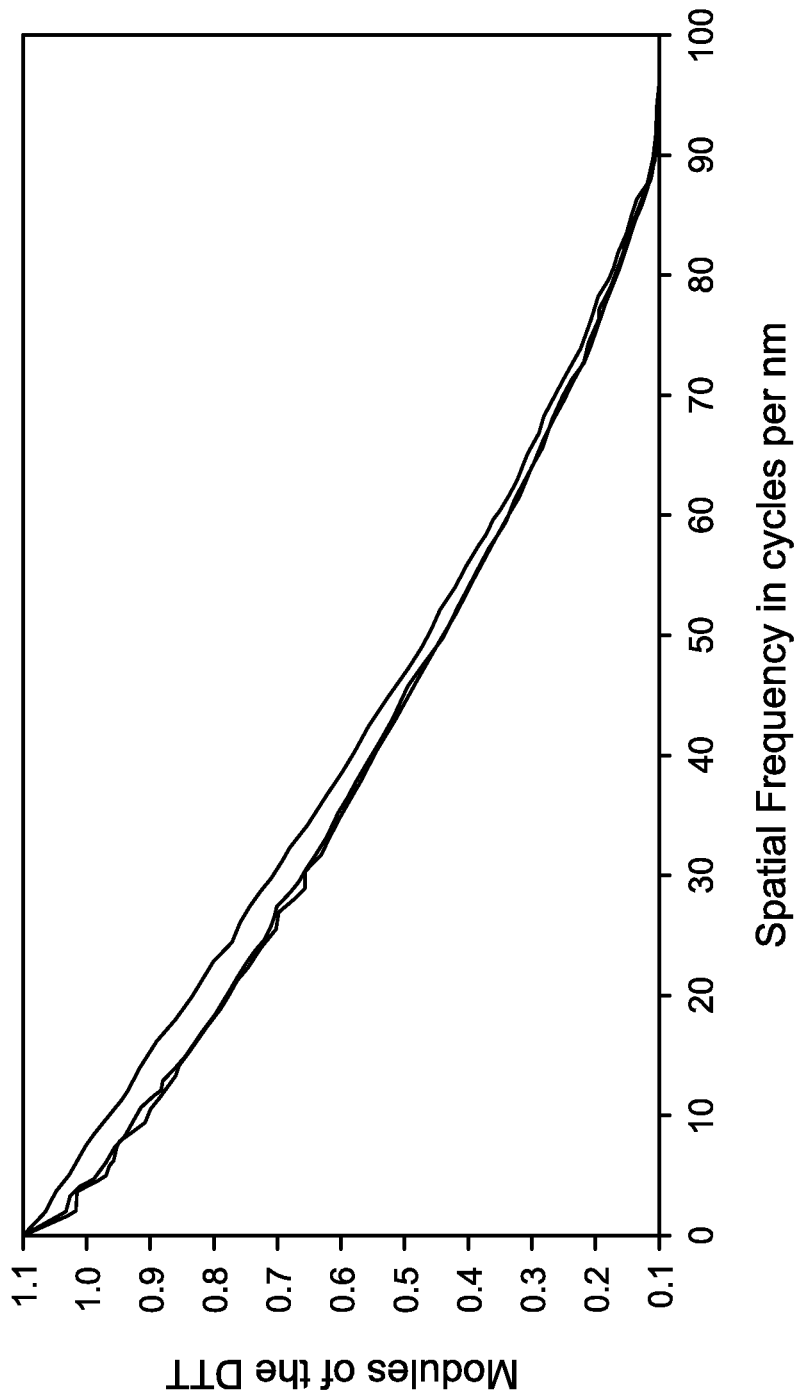
Figure 11C:
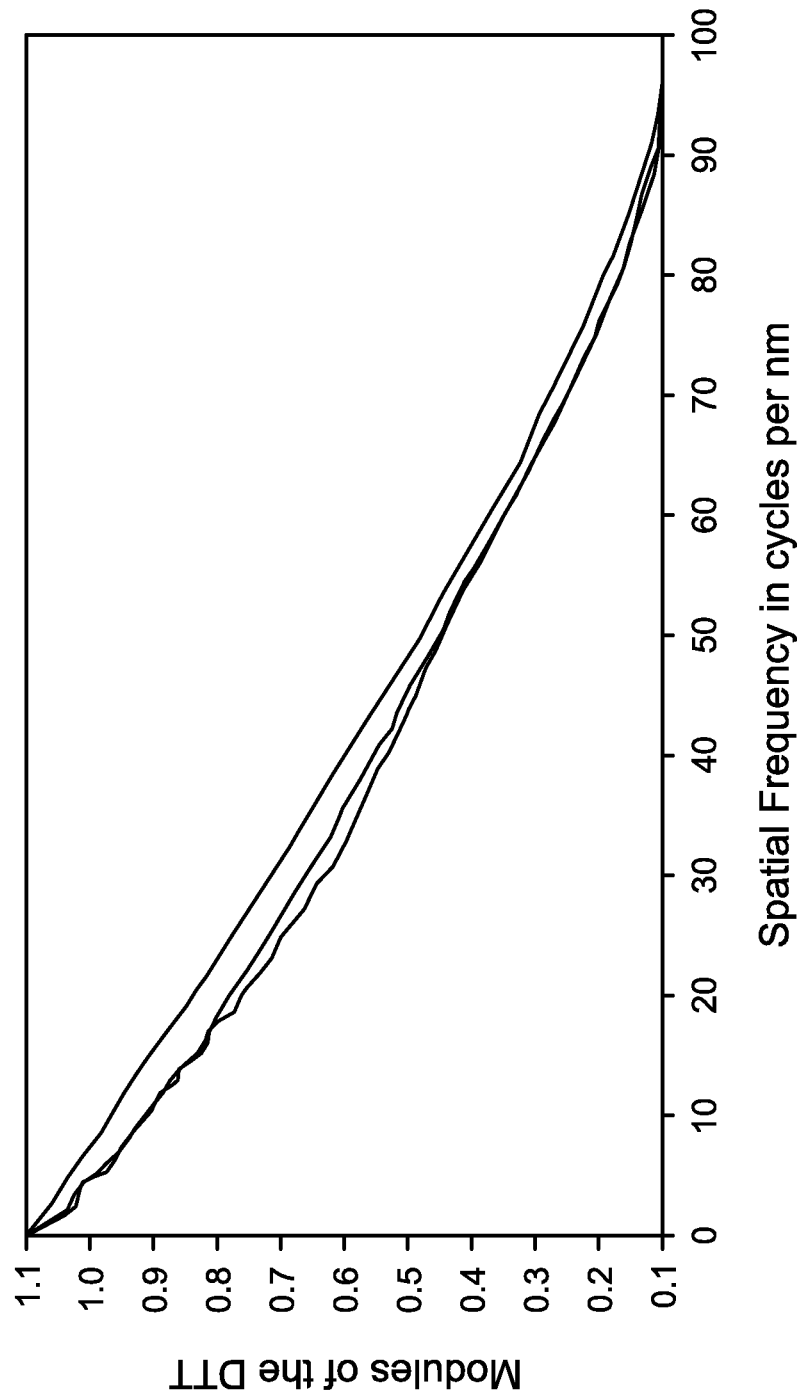

With reference now to FIG. 11, an exemplary simulation depicts the optical power of the exemplary IOL 910 in its resting state (FIG. 11A), in its accommodated state upon implantation (FIG. 11B), and its disaccommodated state (FIG. 11C). In its resting state (e.g., without substantial external forces applied thereto, prior to implantation), the IOL 910 exhibits an optical power of 34 diopter. Upon implantation of the IOL 910, which as discussed above can compress the IOL 910 slightly so as to ensure stability and/or prevent movement (e.g., rotation) of the IOL 910 within the capsular bag, the IOL 910 exhibits an optical power of 31.9 D at an axial compression of 320 μm, as shown in FIG. 11B. Further compression to 460 μm further decreases the focusing power (for far vision) to 29.5 D, as shown in FIG. 11C.

In use, the exemplary accommodative intraocular lenses described herein are adapted to be inserted in the human eye using conventional surgical techniques modified in accordance with the present teachings. Typically, the natural crystalline lens is first removed and the IOL can be folded into a compact size for insertion through an incision or opening in the capsular bag. Following insertion, the single piece IOL (e.g., IOL 10) can be manipulated to assume its proper position in the capsular bag, as described above. An IOL in which multiple components are delivered to the capsular bag independently can be assembled in situ, for example, by sandwiching a solid lens 860 between the optical membranes 822, 824 and coupling the components to one another. In some aspects, the IOLs described herein can be implanted in the capsular bag without optical fluid contained within the cavity such that the method for implantation can further include filling the cavity with the optical fluid while the IOL is disposed within the eye (e.g., via injection). In this manner, implantation of the exemplary IOLs described herein can aid in restoring natural vision by providing an accommodative, curvature-changing refractive lens that mimics how the natural crystalline lens changes shape in response to movement of the ciliary bodies to variously bend incoming light onto the retina depending on the desired focal point. The term intraocular lens or "IOL" is used herein to refer to any lens or lens component adapted to be inserted into a patient's eye. Such a lens can be phakic or aphakic (also referred to in the art as pseudophakic) to restore, improve, or partially correct vision. Phakic lenses are used in conjunction with the natural lens of an eye to correct refractive errors such as myopia (near-sightedness), hyperopia (far-sightedness) and astigmatism, coma or other higher order refractive errors (blurred vision due to poor light focusing on the retina due to an irregularly shaped cornea or, in some instances, an irregularly shaped natural lens). An aphakic or pseudophakic lens is inserted in the eye subsequent to removal of the natural lens due to disease, e.g., a cataract or clouding of the natural lens. The aphakic or pseudophakic lens can also restore, improve, or partially correct vision by providing a power comparable to that of the natural lens and can also correct myopia, hyperopia or other refractive errors. Either type of lens may be implanted in the anterior chamber in front of the iris or in the posterior chamber behind the iris and in front of the natural lens or in the region where the natural lens was before removal.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An intraocular lens configured to be implanted within a capsular bag of a patient's eye, the lens comprising:
   a fluid optic body, comprising:
      an anterior optical membrane configured to extend across an optical axis of the patient's eye;
      a posterior optical membrane configured to extend across the optical axis of the patient's eye;
      a sidewall extending between the anterior optical membrane and the posterior optical membrane, wherein the anterior optical membrane, the posterior optical membrane, and the sidewall define a cavity for containing an optical fluid;
   a plurality of lever arms extending from the sidewall of the optic body, each of the plurality of lever arms extending anteriorly from the sidewall such that at least a portion of each of the plurality of lever arms extends anteriorly beyond the anterior optical membrane while no portion of each of the plurality of lever arms extends posteriorly beyond the posterior optical membrane, wherein each of the plurality of lever arms is configured to be in contact with an anterior surface of the capsular bag such that axial compression of the capsular bag causes each of the plurality of lever arms to rotate posteriorly about a corresponding pivot so as to modify a curvature of the anterior optical membrane; and
   an additional plurality of lever arms extending from the optic body, at least a portion of each of the additional plurality of lever arms extending posteriorly beyond the posterior optical membrane and configured to be in contact with the capsular bag such that the axial compression of the capsular bag causes each of the additional plurality of lever arms to rotate anteriorly about pivots corresponding to each of the additional plurality of lever arms so as to modify a curvature of the posterior optical membrane.

2. The intraocular lens of claim 1, wherein the anterior optical membrane has a smaller radius of curvature when the axial compression of the capsular bag causes each of the plurality of lever arms to rotate posteriorly about the corresponding pivot.

3. The intraocular lens of claim 1, wherein each of the plurality of lever arms is biased to rotate anteriorly about the corresponding pivot upon relaxation of the axial compression.

4. The intraocular lens of claim 1, wherein each of the plurality of lever arms comprises a surface configured to be in contact with the capsular bag, the surface of each of the lever arms being curved.

5. The intraocular lens of claim 1, wherein the plurality of lever arms comprises at least six lever arms.

6. The intraocular lens of claim 1, wherein rotation of each of the plurality of lever arms about the corresponding pivot causes deformation of the sidewall.

7. The intraocular lens of claim 6, wherein the deformation of the sidewall causes the curvature of the anterior optical membrane to be modified.

8. The intraocular lens of claim 1, wherein a distance between the anterior optical membrane and the posterior optical membrane along the optical axis decreases in response to the axial compression.

9. The intraocular lens of claim 1, wherein the plurality of lever arms and the additional plurality of lever arms are offset from one another about a circumference of the optic body.

10. The intraocular lens of claim 1, wherein each of the plurality of lever arms extend from the sidewall to a terminal end, wherein terminal ends of adjacent lever arms are coupled to one another via a ring.

11. The intraocular lens of claim 1, wherein the posterior optical membrane is configured to be disposed in contact with a posterior surface of the capsular bag.

12. The intraocular lens of claim 1, wherein each of the plurality of lever arms has an anterior-most surface between the sidewall and the terminal end, the anterior-most surface of each of the lever arms configured to be in contact with the anterior surface of the capsular bag.

13. The intraocular lens of claim 1, wherein the sidewall is concave relative to the optical axis.

* * * * *